(12) United States Patent
Boehm et al.

(10) Patent No.: US 8,006,698 B2
(45) Date of Patent: Aug. 30, 2011

(54) AEROSOL THERAPY DEVICE

(75) Inventors: Andreas Boehm, Reichling (DE);
Martin Luber, Munich (DE); Sven Rosenbeiger, Starnberg (DE)

(73) Assignee: PARI GmbH Spezialisten fuer effektive Inhalation, Starnberg (DE)

( * ) Notice: Subject to any disclaimer, the term of this patent is extended or adjusted under 35 U.S.C. 154(b) by 767 days.

(21) Appl. No.: 11/650,817

(22) Filed: Jan. 8, 2007

(65) Prior Publication Data
US 2007/0181133 A1 Aug. 9, 2007

(30) Foreign Application Priority Data
Jan. 9, 2006 (DE) .......................... 10 2006 001 113

(51) Int. Cl.
*A61M 15/08* (2006.01)
*A61M 15/00* (2006.01)
*A61M 16/00* (2006.01)
*A62B 18/02* (2006.01)

(52) U.S. Cl. ......... 128/207.18; 128/201.18; 128/203.12; 128/203.15; 128/206.11; 128/200.24

(58) Field of Classification Search ............ 128/200.11, 128/200.12, 200.13, 200.14, 200.16, 200.18, 128/200.23, 200.24, 203.12, 203.15, 203.16, 128/203.17, 203.18, 203.19, 203.21, 203.22, 128/204.12, 206.29, 207.13, 207.18; 239/330, 239/310, 322, 338, 350, 337, 586; 222/386, 222/378, 321.1, 321.6, 321.7, 321.8, 381, 222/391, 327, 326, 160, 162, 163; 604/151, 604/207, 211, 131, 209, 232, 208; 606/199, 606/204.45

See application file for complete search history.

(56) References Cited

U.S. PATENT DOCUMENTS

| | | | | |
|---|---|---|---|---|
| 2,078,180 | A | * 4/1937 | Kronenberg | .................... 604/28 |
| 2,582,529 | A | 1/1952 | Curry et al. | |
| 4,029,095 | A | * 6/1977 | Pena | .............................. 604/30 |
| 4,268,460 | A | * 5/1981 | Boiarski et al. | .................... 261/1 |
| 4,273,124 | A | * 6/1981 | Zimmerman | ............ 128/207.18 |
| 4,429,835 | A | 2/1984 | Brugger et al. | |
| 4,951,661 | A | * 8/1990 | Sladek | ..................... 128/202.27 |
| 5,054,477 | A | * 10/1991 | Terada et al. | ............. 128/200.14 |
| 5,584,285 | A | * 12/1996 | Salter et al. | ............... 128/200.21 |
| 5,687,715 | A | 11/1997 | Landis et al. | |
| 5,871,009 | A | * 2/1999 | Rydgren et al. | ......... 128/203.12 |

(Continued)

FOREIGN PATENT DOCUMENTS
DE 32 38 149 A1 4/1984
(Continued)

OTHER PUBLICATIONS

Search report mailed Jul. 6, 2007 from European Application No. 07007418.2.

(Continued)

*Primary Examiner* — Justine R Yu
*Assistant Examiner* — Annette F Dixon
(74) *Attorney, Agent, or Firm* — Wolf, Greenfield & Sacks, P.C.

(57) ABSTRACT

The invention regards a therapeutic aerosol device in which a main aerosol flow, which is generated with the help of a compressed gas and is supplied to one of the nostrils of a user, is superimposed by pressure fluctuations. The superimposition of the pressure fluctuations occurs directly at one of the two nostrils of the user. A flow resistance is provided in the other nostril.

26 Claims, 7 Drawing Sheets

U.S. PATENT DOCUMENTS

| | | | |
|---|---|---|---|
| 5,890,491 A * | 4/1999 | Rimkus | 128/206.11 |
| 5,928,190 A * | 7/1999 | Davis | 604/94.01 |
| 6,636,767 B1 | 10/2003 | Knudson et al. | |
| 6,715,485 B1 | 4/2004 | Djupesland | |
| 7,059,320 B2 | 6/2006 | Feiner et al. | |
| 7,225,807 B2 | 6/2007 | Papania et al. | |
| 2006/0162722 A1 | 7/2006 | Boehm et al. | |

FOREIGN PATENT DOCUMENTS

| | | |
|---|---|---|
| DE | 36 17 400 A1 | 11/1987 |
| DE | 200 19 479 U1 | 3/2001 |
| EP | 0 507 707 B1 | 10/1992 |
| EP | 0 652 021 A1 | 5/1995 |
| EP | 0 732 111 A2 | 9/1996 |
| EP | 1 180 378 A2 | 2/2002 |
| FR | 1 567 403 | 5/1969 |
| FR | 2 639 236 A1 | 5/1990 |
| WO | WO 00/51672 A1 | 9/2000 |
| WO | WO 01/02024 A1 | 1/2001 |
| WO | WO 01/34232 A1 | 5/2001 |
| WO | WO 03/082393 A1 | 10/2003 |
| WO | WO 2004/004814 A2 | 1/2004 |
| WO | WO 2004/020029 A1 | 3/2004 |

OTHER PUBLICATIONS

Extended Search Report issued on Jun. 3, 2008 from corresponding European Application No. 1 806 157.

H. Kauf, "Ability of Aerosols to Penetrate Paranasal Sinuses", Archiv klin. expert Ohren-, Nasen-und Kehlkopfheilk., 190, pp. 95-108, 1968.

Hyo et al., Particle deposition efficiency of therapeutic aerosols in the human maxillary sinus, Rhinology, 27, pp. 17-26, 1989.

Search report mailed Dec. 12, 2003 from International Application No. PCT/EP03/09862.

Office Action cited in U.S. Appl. No. 10/519,011.

* cited by examiner

AEROSOL THERAPY DEVICE

FIELD OF INVENTION

The invention relates to an aerosol therapy device, in which an aerosol generated in a nebulizing device is supplied through a nosepiece to a patient's nasal cavities in the form of a main aerosol flow.

BACKGROUND

Known in this context from "*Eindringvermögen von Aerosolen in Nebenräume*", H. Kauff, Archiv. klin. exper. Ohren-, Nasen- and Kehlkopfheilk. 190, 95-108 (1968), is that pressure fluctuations and vibrations can cause aerosol to penetrate the paranasal sinuses, through which the main aerosol flow through the nasal cavities does not otherwise actively flow. An example of these realisations is known from EP 0 507 707 A1. According thereto, an aerosol flow is superimposed with pressure fluctuations which are supposed to cause the aerosol particles/droplets in the main aerosol flow to pass through the ostia and enter the paranasal sinuses. In this way, even though the main aerosol flow does not directly flow through the paranasal sinuses, they can be reached and treated by a drug administered in aerosol form. As also with other types of aerosol therapy, it is attempted to deposit sufficient quantities of the drug at the desired points, for which in the case of the paranasal sinuses a sufficient quantity of the aerosol of the main aerosol flow must pass through the ostia and penetrate the paranasal sinuses.

Experimental tests on different models of the human nose have demonstrated that when known aerosol therapy devices are used, deposition in the paranasal sinuses is less than expected and desired. The opening size of the ostia, which is often very small as a result of the disease, also has a great influence on deposition.

Known from DE 102 39 321 B3 is an aerosol therapy device of the type described above, comprising a nebulizer having an aerosol generator to which compressed air is supplied for the generation of a main aerosol flow and having a connector for supplying pressure fluctuations which are superimposed on the main aerosol flow, and a nosepiece for supplying the aerosol to one of the two alae of the nose, which is connected to the nebulizer. A flow resistance device is furthermore provided, by means of which the flow resistance at the other of the two alae of the nose of the user is precisely defined. Owing to the flow resistance at the other nostril, the superimposed pressure fluctuations cause to a greater extent the aerosol of the main aerosol flow to also reach the paranasal sinuses and deposition of the aerosol there.

However, the supply of the flow of compressed gas and pressure fluctuations described in DE 102 39 321 B3 requires a specific design of the nebulizer, and thus not every nebulizer is suitable for this use.

SUMMARY OF THE INVENTION

Against this background, the object of the invention is to disclose suitable measures by means of which other nebulizers can also be used in an aerosol therapy of the type described above with almost the same or better deposition of the aerosol in the paranasal sinuses in order to achieve therapeutically useful and predictable deposition in the paranasal sinuses through which there is no active flow also with other nebulizers.

This object is achieved by an aerosol therapy device comprising: a) a nebulizer device, to which a compressed gas, preferably compressed air, can be supplied, having an aerosol generator for the generation of an aerosol which together with the supplied compressed gas forms an main aerosol flow, b) a nosepiece connected with the nebulizer device for supplying the aerosol to one of the two nostrils of the nose of a user, c) a flow resistance device for provision of a flow resistance in the other of the two nostrils of the user, and d) a connection device for the supply of pressure fluctuations which are superimposed on the main aerosol flow, the connection device being formed such on the nosepiece or the flow resistance device that the pressure fluctuations are introduced directly into the respective nostril of the user's two nostrils.

A device configuration according to the invention is in particular characterised in that diseases of the upper and lower respiratory tract can be directly treated therewith if they have a nasal or paranasal cause.

It is furthermore characteristic of a device configuration according to the invention that liquid medicinal formulations can thus be particularly advantageously deposited in the paranasal cavities in the form of an aerosol mist in order to treat diseases whose cause is there.

Furthermore, a device configuration according to the invention is also characterised in that illnesses such as chronic or allergic sinusitis, inflammations or other infections or conditions ("atrophic rhinitis") can also be topically treated as a result of the targeted deposition of active ingredients in the nose and paranasal cavities, to thereby avoid unwanted side effects of a symptomatic medicinal therapy.

BRIEF DESCRIPTION OF THE DRAWINGS

The invention will be described in more detail below by means of embodiments and referring to the drawings.

DETAILED DESCRIPTION

Figure 1:
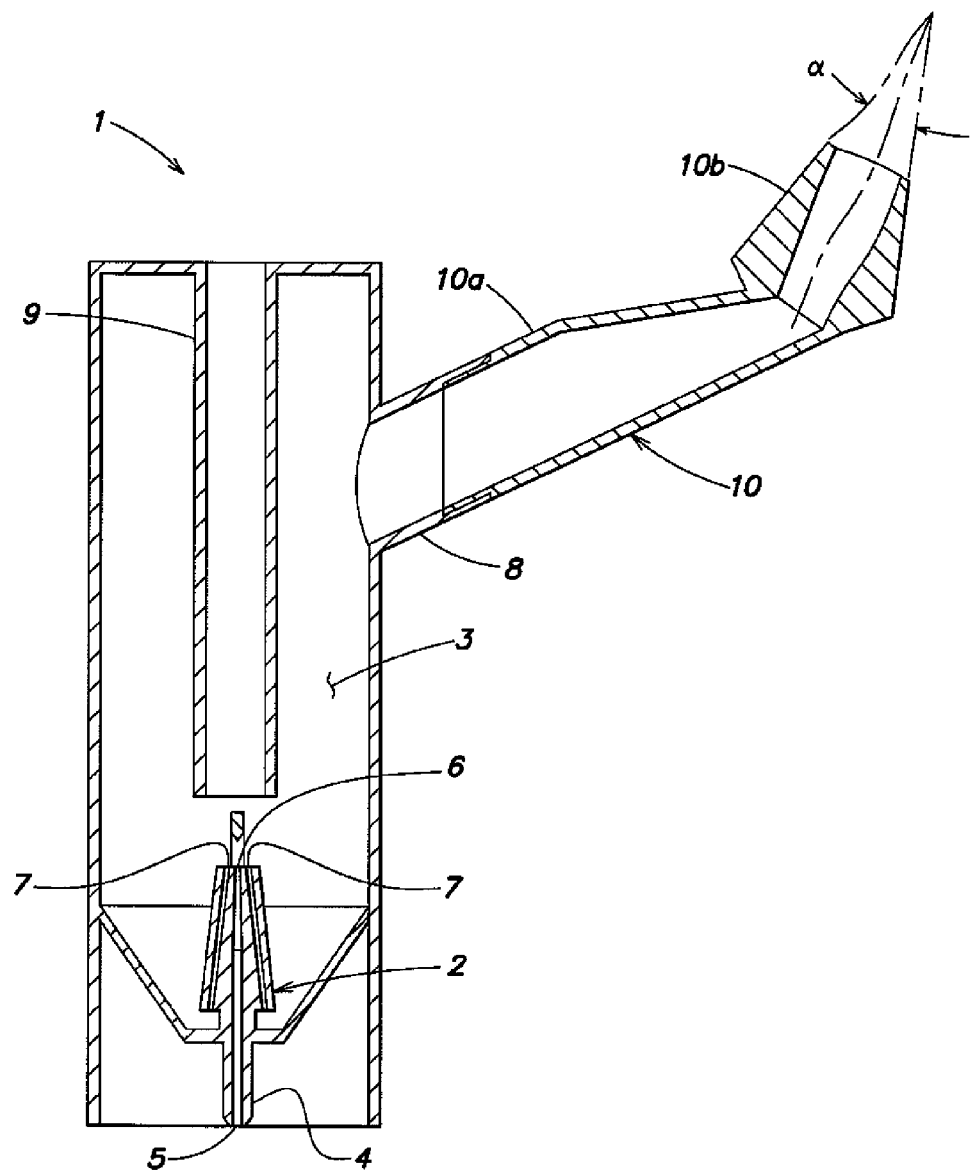
FIG. 1 shows a view of a first nebulizing device for use in an aerosol therapy device according to the invention.

FIG. 1 shows a first example of a nebulizing device which can be used, within the scope of the invention, for an aerosol therapy as described above. The nebulizing device 1 comprises an aerosol generator 2 arranged in a nebulizing chamber 3. A liquid stored at the bottom of the aerosol generator is nebulized by means of the aerosol generator 2 when compressed air is supplied to the aerosol generator 2 via a connector 4 arranged at one end (at the bottom of FIG. 1) of the aerosol generator. The compressed air flows through a compressed air channel 5 arranged centrally in the aerosol generator and emerges at the other end of the aerosol generator through a nozzle opening 6. The liquid is drawn in through suction channels 7, which are arranged next to the compressed air channel and extend in the aerosol generator from the level of the nozzle opening to the bottom of the aerosol generator and open up towards the liquid stored there, and is nebulized into the nebulizing chamber 3 in the area in front of the nozzle opening 6.

In the case of aerosol therapies directed at the lower respiratory tract, the bronchial tract and the lungs, a patient inhales the aerosol generated in this manner by taking in the aerosol from the nebulizing device upon inhalation via a mouthpiece attached to a connecting piece 8 on the nebulizing device. Hereby, ambient air flows through an air inlet flue 9 as required into the nebulizing chamber 3 when the aerosol is withdrawn from the nebulizing chamber 3 during the inhalation phase.

Figure 8:
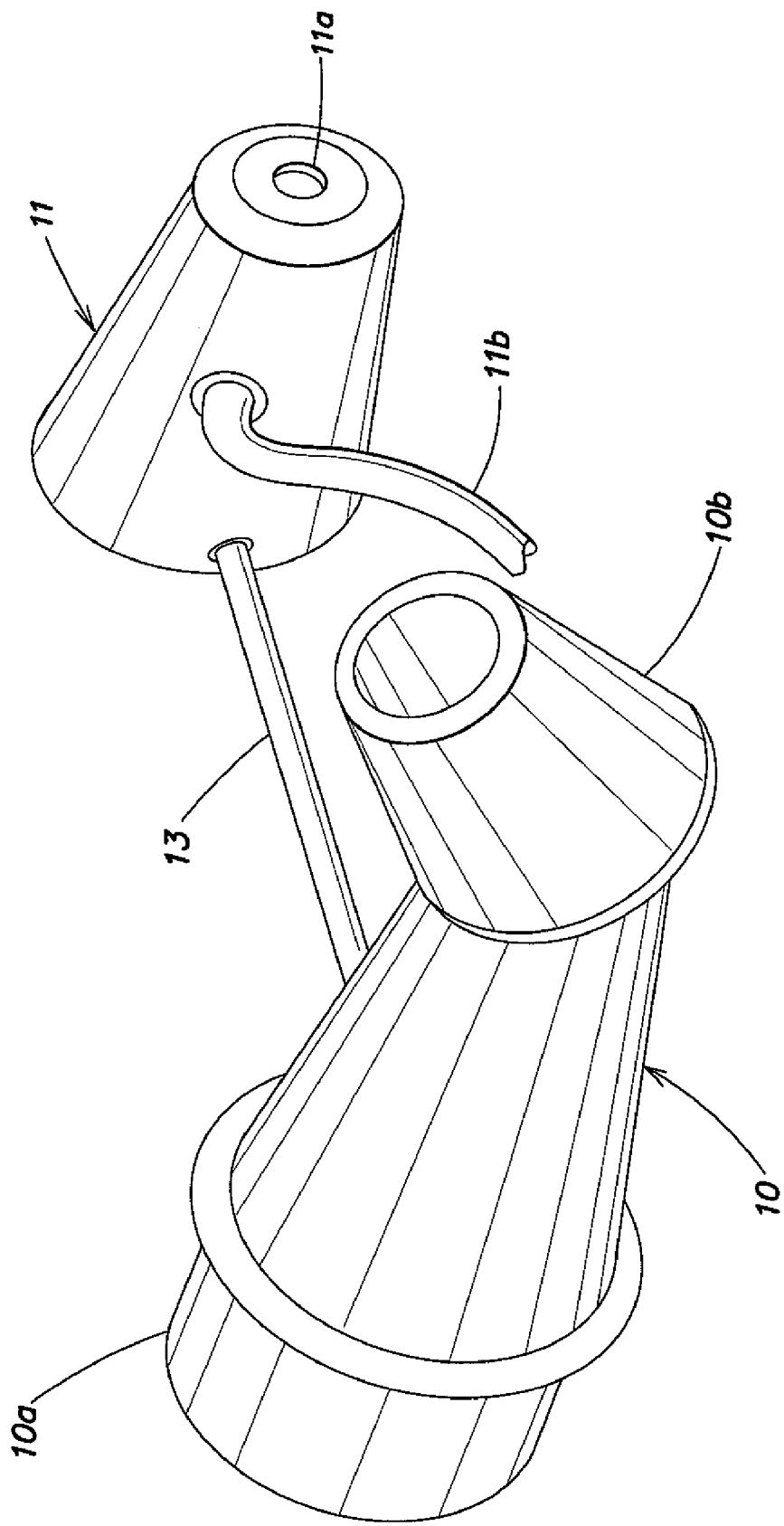
FIG. 8 shows a view of a nosepiece with a connected flow resistance device.

In the case of aerosol therapies directed at the nasal cavity, the mouthpiece is replaced by a nosepiece 10 configured at one end 10*a* for attachment to the connecting piece 8 on the nebulizing device 1 while the other end 10*b* is designed so that it may be introduced in a nostril of a patient's nose and seal it tightly. The end 10*b* preferably takes the shape of a truncated cone with an aperture angle α in a range of 10° to 40°. Hereby, the longitudinal axis of the truncated cone is inclined in relation to the longitudinal axis of the connecting piece 8 so that, when the nebulizer is held vertically, it is ensured that the nosepiece may be placed simply and comfortably in the patient's nostril. Reference is furthermore made to FIG. 8 as regards the previous description of the nosepiece 10.

In this manner, the aerosol generated in the nebulizing device is supplied to one nostril and hence one nasal cavity of the patient. The compressed air supplied to the nebulizing device for the generation of the aerosol, ensures that there is a sufficient main aerosol flow in or through the patient's nose. The main aerosol flow passes from the one nostril through the one nasal cavity to the other nasal cavity. This main aerosol flow is superimposed by pressure fluctuations as will be described in more detail below. Without further measures, the main aerosol flow emerges from the other nostril of the patient's nose when the patient, as is common in aerosol therapies for nasal cavities, seals the nasal cavities from the throat and mouth by means of the soft palate.

In the first example of a nebulizing means that is suitable for the use of the invention as described above, a main aerosol flow is also produced quasi as a result of the system owing to the supply of compressed gas for aerosol generation. The compressed gas flow can be at least used to generate the desired main aerosol flow. However, other nebulizing devices generate an aerosol without the supply of compressed gas, for example by means of an oscillating membrane or a ultrasonic oscillator. In these cases, a main aerosol flow has to be generated according to the invention using additional measures. An example of a nebulizing device of the latter type and suitable measures for generating a main aerosol flow will be described in the following.

Figure 2:
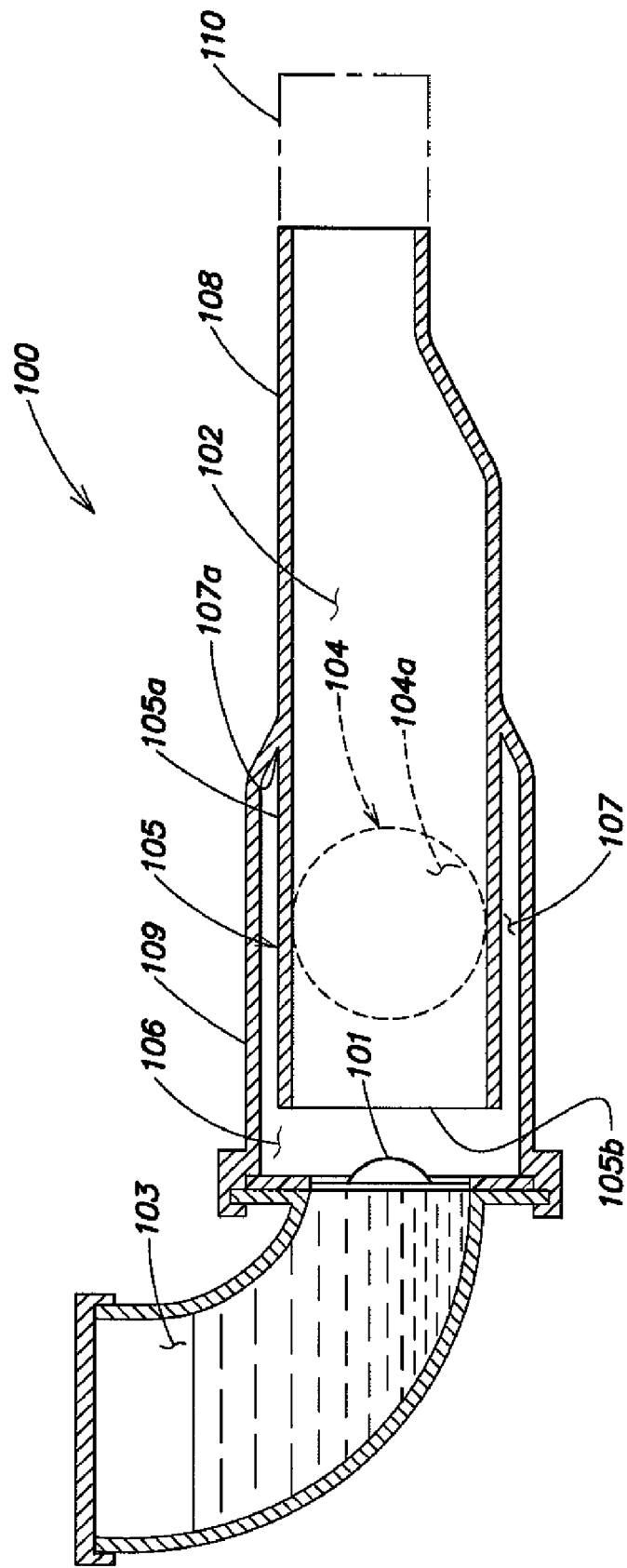
FIG. 2 shows a first view of a second nebulizing device for use in an aerosol therapy device according to the invention.
Figure 3:
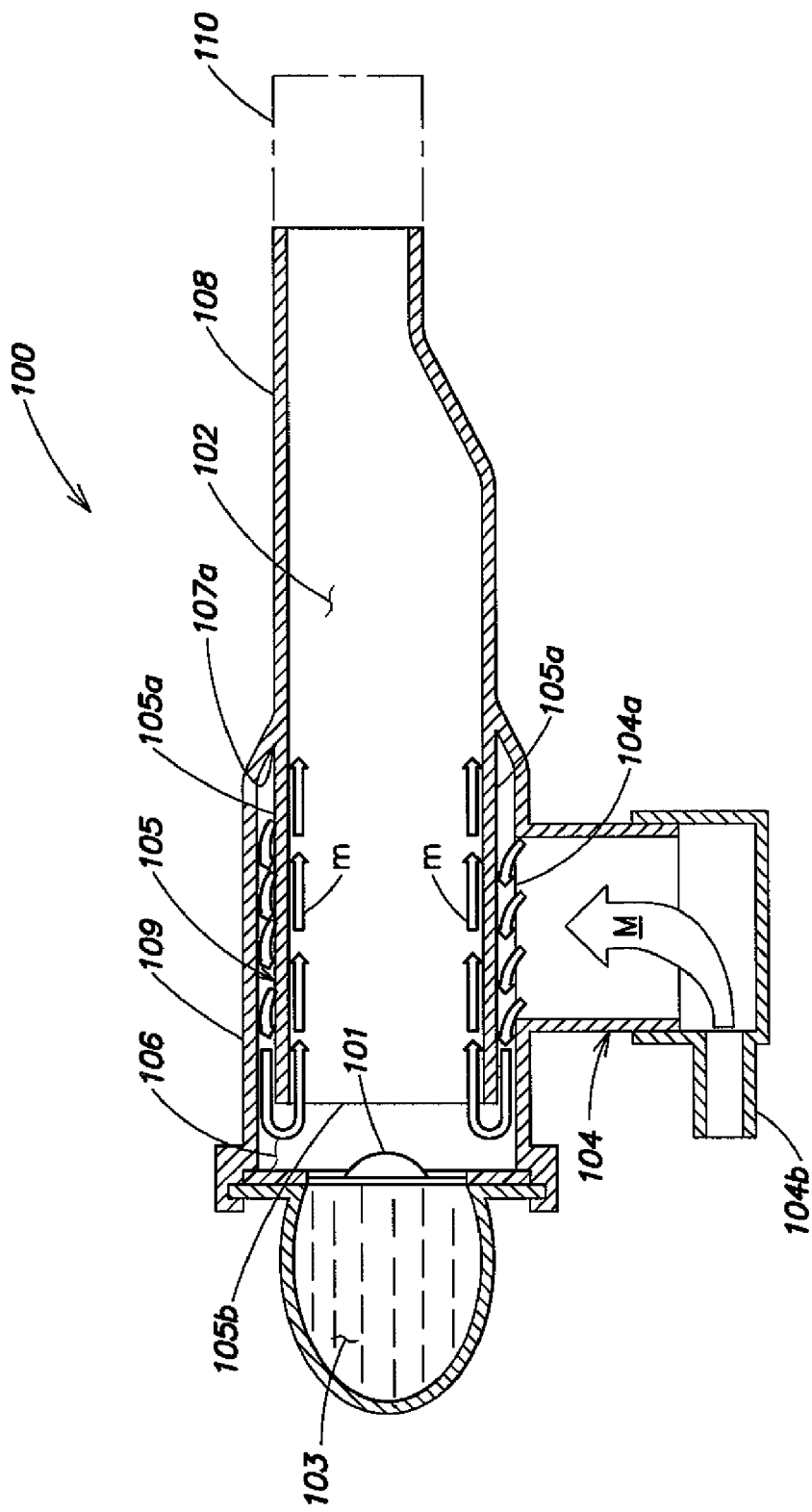
FIG. 3 shows a second view of the second nebulizing device for use in an aerosol therapy device according to the invention.

This second example of a nebulizing means that is suitable for the use of the invention is explained by means of FIGS. 2 and 3, which both show a cut view of the nebulizing device, however from different angles.

Shown in FIGS. 2 and 3 is a nebulizing device 100 comprising an aerosol generator 101, for example a membrane aerosol generator. The liquid to be nebulized is stored in a liquid reservoir 103 and is supplied to the aerosol generator 101. The aerosol generator 101 generates an aerosol from the supplied liquid, which is released into an expansion spatial area 102. In particular in membrane aerosol generators, generation and release of the aerosol occurs in the form of an aerosol cloud expanding to a certain extent in a specific direction, which expands from the aerosol generator 101 into the expansion area 102.

The nebulizing means 100 furthermore comprises a supply means 104 for supplying a pressurised gaseous medium, in particular air, a therapeutically effective gas or a gas suitable for diagnosis. The flow of compressed gas is supplied to the inhalation therapy device 100 via the supply means 104 such that a main aerosol flow can arise, as will be explained below.

In the nebulizing device 100 as shown in FIGS. 2 and 3, the compressed gas supplied via the supply means 104 impinges upon a flow influencing means 105. The flow of the supplied gaseous medium M is influenced by the flow influencing means 105 in such a manner that the gaseous medium M forms a sheath flow m around the expansion area 102 for the aerosol and transports the aerosol to the patient, forming thereby a main aerosol flow. The flow of the supplied gaseous medium M is indicated as an example in the plane of the drawing in FIG. 3. FIG. 3 furthermore shows several arrows which represent the supplied gaseous medium M, which disperses around the flow influencing means 105 and circulates around the flow influencing means such that it finally flows along the rim of the expansion spatial area 102 in which the aerosol cloud released by the aerosol generator 101 essentially disperses centrally. As can be easily seen in particular from FIG. 3, the desired main aerosol flow that is directed towards the connecting piece 108 for a nosepiece 110 arises in this way since the supplied compressed gas can only escape from the nebulizing device 100 in this manner. It carries the generated aerosol with it and conveys it to the connecting piece 108 for the nosepiece 110.

As regards the nosepiece 110, which is not explicitly shown in FIGS. 2 and 3, reference is made to the description of the nosepiece 10 in FIG. 1 above and to the representation in FIG. 8.

In nebulizing device shown in FIGS. 2 and 3, the flow influencing means is realised in the form of a cylindrical tube piece 105 which is disposed around the expansion spatial area 102. The aerosol cloud generated by the aerosol generator expands into the cylindrical tube piece 105. As can furthermore be seen from FIGS. 2 and 3, the cylindrical tube piece has a circular cross-section in the shown embodiment, which is both expedient and advantageous. The supplied compressed gas M impinges upon the outer sheath surface 105*a* of the tube piece 105. It flows along the outer sheath surface 105*a* around the cylindrical tube piece 105, and thereby expands in the direction of the front end 105*b* of the tube piece 105. Owing to the deflection and redirection of the flow of the gaseous medium M, the gaseous medium M is essentially distributed evenly around the cylindrical tube piece 105 and reaches the front end 105*b*, which is disposed opposite the aerosol generator 101, so that the gaseous medium flows around the front end 105*b* of the tube piece 105 and in the rim region of the expansion zone 102 of the aerosol cloud, flows further along the inner surface of the tube piece 105. A cylindrical sheath flow m thereby forms around the expansion spatial area 102 for the aerosol.

As is shown in FIGS. 2 and 3, the tube piece 105 in the shown example of a nebulizing device 100 is configured integrally with the connecting piece 108 for a nosepiece 110, via which the aerosol conveyed in the main aerosol flow is supplied to the nose of a patient.

In the example of a nebulizing device 100 shown in FIGS. 2 and 3, the cylindrical tube piece 105 is disposed in a chamber 106, into which the aerosol generator 101 releases the aerosol. The chamber 106 is surrounded by a section 109 of the housing of the nebulizing device 100, with the housing section 109, similar to the cylindrical tube piece 105, having a cylindrical, for example an annular cylindrical, cross-section. Since the gap region 107 is terminated in an area 107a that is disposed at a distance from the aerosol generator 101, the expansion of the gaseous medium M occurs in the direction of the end face 105b of the tube piece 105, which is opposite the aerosol generator 101.

It can further be seen from FIGS. 2 and 3 with regard to the explained example of a nebulizing device 100 that the supply means for the gaseous medium M is preferably a cylindrical connecting piece 104, which is provided on the housing 109 of the nebulizing device 100 and opens in the direction of the chamber 106. The outlet 104a of the cylindrical connecting piece 104 is thereby arranged so that it is aligned on the tube piece 105 in such a manner that this tube piece has a deflective and redirectional effect on the gaseous medium M.

The position of the outlet 104a and the cylindrical connecting piece 104 is indicated in FIG. 2 by a dashed line. It can be seen from this figure that the cylindrical connecting piece 104 preferably has a circular cylindrical cross-section and is disposed centrally to the cylindrical tube piece 105. The connecting piece 104 can, however, also have a different cross-section, for example an elliptical cross-section, and/or can be disposed eccentrically to the tube piece 105.

The supply means 104 of the shown example of a nebulizing device 100 furthermore comprises a connecting piece 104b for connecting a line, for example a hose. The compressed gas M is supplied via the hose.

The two examples described above show that a nebulsing device is suitable for use in an aerosol therapy as described at the start of this application if, owing to the supply of compressed gas, a main aerosol flow is generated, which transports the aerosol generated by an aerosol generator of the nebulizing device to a nosepiece of the nebulizing device such that it can be supplied to the opening of an ala of the nose of a patient via the nosepiece.

Figure 4:
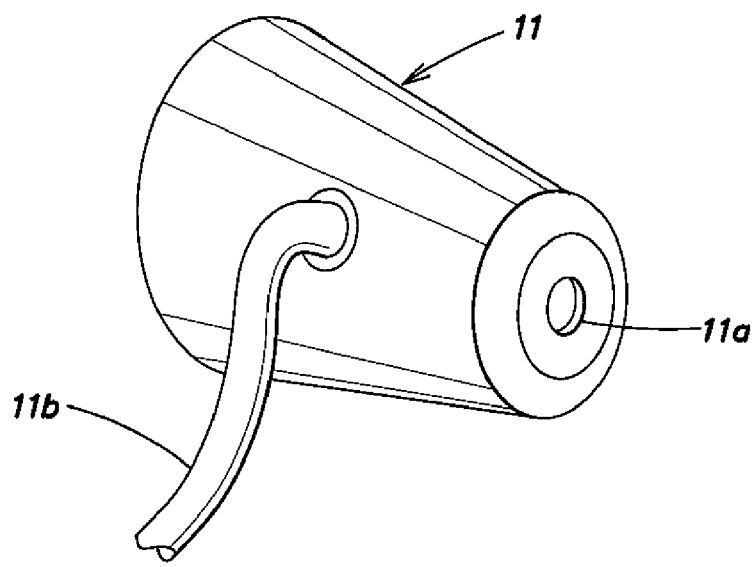
FIG. 4 shows a view of a flow resistance device according to the invention.
Figure 5:
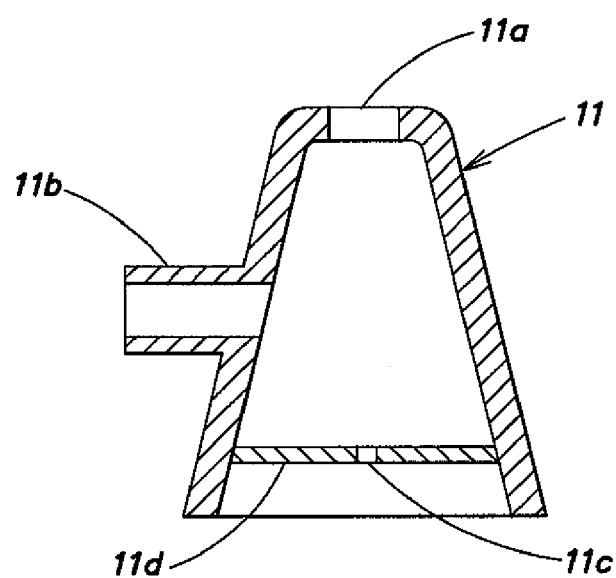
FIG. 5 shows a further view of the flow resistance device according to the invention.

According to one aspect of the invention described herein, a flow resistance device 11 is to be provided in the opening of the other ala of the nose of the patient, which is shown in FIGS. 4 and 5. The flow resistance means 11 has a first opening 11a, a connecting means 11b and a flow resistance 11c, for example in the form of a second opening 11c which is smaller than the first opening. The flow resistance realised in this manner is greater than the resistance of the natural flow path through the patient's nose. It is only with the significantly higher flow resistance at the other nostril and hence at the other end of the flow path of the main aerosol flow through the patient's nose that an effective quantity of the aerosol is able to penetrate the paranasal sinuses.

The pressure fluctuations that are necessary for penetration of the aerosol into the paranasal sinuses are impressed upon the main aerosol flow via the connecting means 11b. The connecting means 11b is connected to a suitable source for pressure fluctuation for this purpose.

Figure 6:
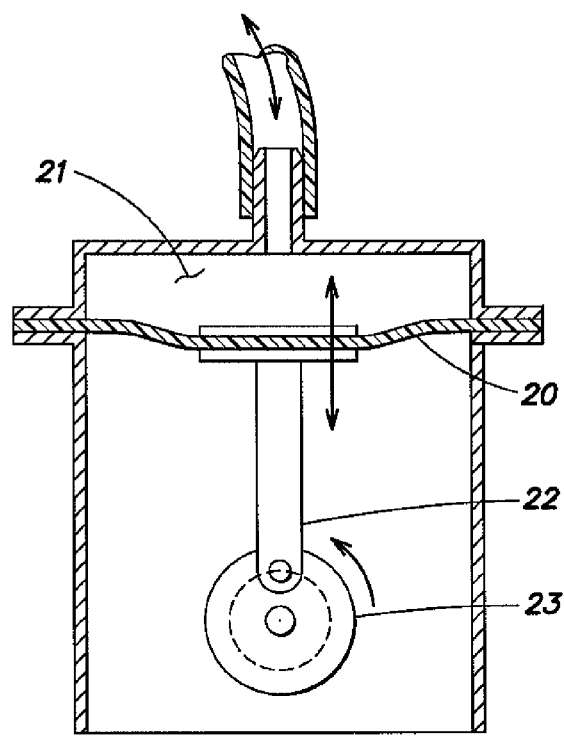
FIG. 6 shows a view of a device for the generation of pressure fluctuations.

The pressure fluctuations impressed upon the main aerosol flow may, for example, be generated in different ways. As shown in FIG. 6, the pressure fluctuations may be generated by means of a membrane 20, which seals a hollow space 21 (pressure chamber) in a pressure-tight manner if the membrane 20 is moved to and fro by a piston rod 22. For this purpose, the piston rod 22 is supported eccentrically on a driving pulley 23 so that the piston rod 22 causes a pressure-fluctuation-generating movement of the membrane 20 when the driving pulley 23 turns. For this purpose, the driving pulley 23 is in turn connected to an electric motor (not shown) or another suitable drive.

The pressure fluctuations reach the interior of the flow resistance means 11 via a hose line connected to the connecting means 11b and the nasal cavities of the patient via the first opening 11a.

Figure 7:
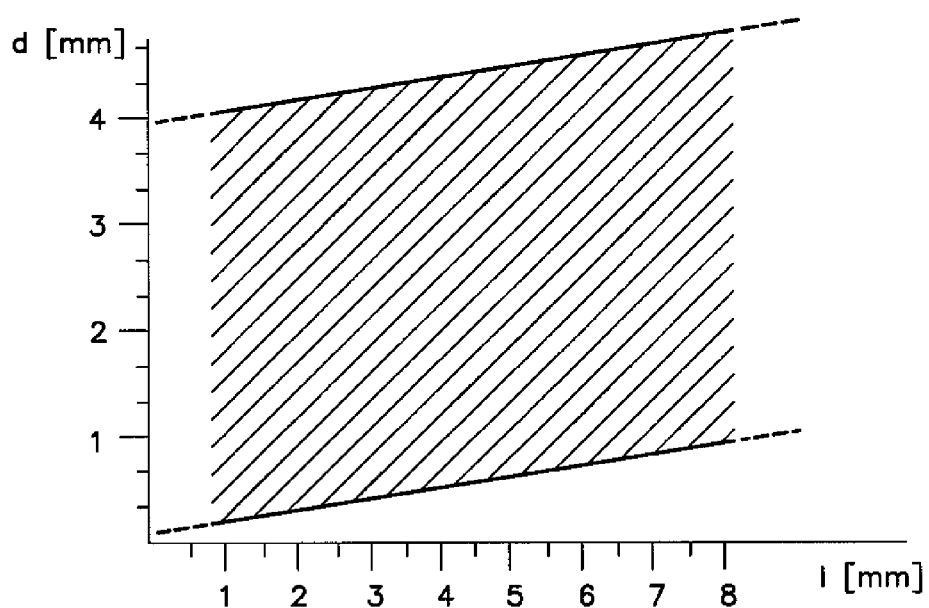
FIG. 7 shows a diagram for determining the effective diameter/length pairs of variants for a flow resistance device according to the invention.

The flow resistance means 11 for a nostril of the patient may be realised, for example, in the form of a stopper 11 with a large first opening 11a and a smaller second opening 11c, the actual flow resistance, as shown in FIGS. 4 and 5. The stopper has a conical basic shape with an aperture angle a in a range of 10° to 40°, which is adapted to the nostrils of the human nose and hence ensures a secure fit. The stopper is preferably hollow as can be seen in FIG. 5, and comprises at the tapered end the first drill-hole 11a which connects the nasal cavities of the patient with the interior of the stopper. The connecting device 11b for the pressure fluctuations also opens out into the interior. The interior is sealed to the outside by a wall 11d, which merely comprises the smaller second drill-hole 11c. The diameter d of the second drill-hole and its length l determine the flow resistance applied against the main aerosol flow and the pressure fluctuation flow. FIG. 7 shows an example of a range of possible pairs of variates of diameter d and length l for the second opening 11c of a flow resistance device according to the invention. Suitable values for d and l can be determined from this range, which is shown with a grey background in FIG. 7.

In order to simplify the handling of the nosepiece 10 and to prevent the stopper 11 being lost, the stopper 11 is preferably connected to the nosepiece 10, as shown in FIG. 8. This can be achieved by means of a flexible connecting element 13 which shows the integral configuration of the nosepiece 10 and the flow resistance device 11 from one and the same material.

Figure 9:
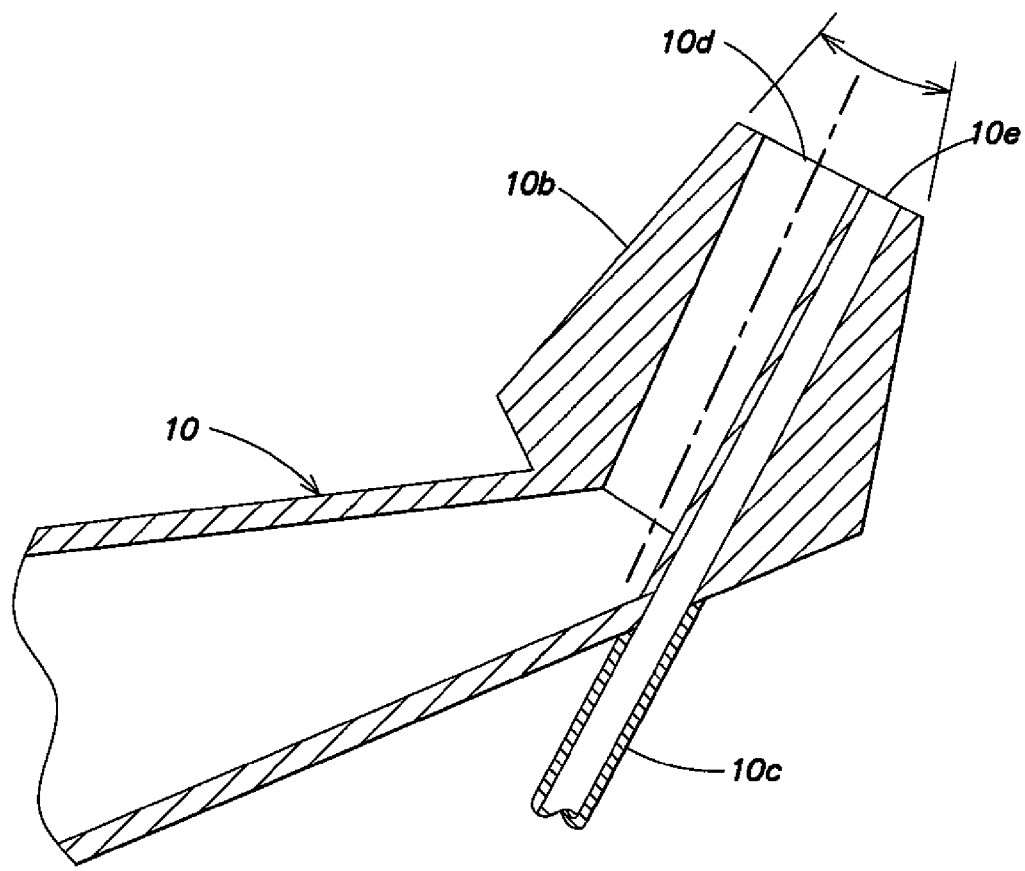
FIG. 9 shows a view of a nosepiece according to the invention for applying pressure fluctuations.

According to another aspect of the invention described herein, as is shown in FIG. 9, the nosepiece 10 is equipped with a connecting means 10c for the supply of pressure fluctuations. In other words, the pressure fluctuations required for the penetration of the aerosol into the paranasal sinuses are impressed on the main aerosol flow at the nostril, to which the main aerosol flow is also applied. The connecting means 10c extends for this purpose up to a main outlet 10d of the nosepiece 10, out of which the main aerosol flow exits. Outlet 10e of the connecting means 10c is disposed there in the immediate vicinity of the main outlet 10d of the nosepiece 10. The pressure fluctuations supplied via the connecting means 10c are thus superimposed on the main aerosol flow. The connecting means 10c is connected for this purpose to a suitable source of pressure fluctuations. Reference is made to the description of FIG. 6 as regards the source of pressure fluctuations.

In the final aspect of the invention last described, a basic flow is expediently added to the pressure fluctuations that are superimposed on the main aerosol flow via the connecting means 10c, by supplying a second flow of compressed gas via the connecting means 10c. The additional flow of compressed gas is significantly lower than the flow of compressed gas that is necessary for the generation of the main aerosol flow through the nasal cavities of the patient. The ratio of the flows between the main aerosol flow and the superimposed additional flow is preferably at least 2:1.

It is common to both aspects of the invention that the supply of the pressure fluctuations occurs directly at one or the other nostril of the patient's nose. According to one aspect of the invention, this occurs by impressing the pressure fluctuations via the stopper, which represents the flow resistance at the nostril, out of which the main aerosol flow exits. According to the other aspect of the invention, the pressure fluctuations are introduced into the nasal cavities of the patient via the end of the nosepiece and are superimposed on the main aerosol flow; the nosepiece is thereby configured similarly to the flow resistance means in the form of a stopper to be inserted into the nostril.

The deposition of the aerosol in the paranasal sinuses can be improved in both aspects of the invention in that the pressure fluctuations are clocked. In other words the pressure fluctuations are not permanently superimposed on the main aerosol flow, but rather only in selected time periods. The triggering or timed clocking of the impressed pressure fluctuations can occur such that the pressure fluctuations are only superimposed after a predetermined period of time after the start of aerosol generation and the main aerosol flow. As this time, the nasal cavities of the patient are filled with aerosol.

It can be easily seen from the previous description of the invention by means of embodiments that an essential advantage of the device configuration according to the invention is that diseases of the upper and lower respiratory tract can be specifically treated if their cause is nasal or paranasal. It is furthermore apparent to the expert reader that a device configuration according to the invention is characterised in that liquid medicinal formulations can be deposited particularly advantageously in the form of an aerosol mist in the paranasal cavities in order to treat illnesses originating there.

These characteristics of the device configuration according to the invention result in that such illnesses such as chronic or allergic sinusitis, inflammations or infections or other illnesses or conditions ("atrophic rhinitis") can be topically treated by the targeted deposition of active ingredients in the nose and paranasal cavities, such that by this means the unwanted side effects of a symptomatic medical therapy can be avoided.

The purpose and object of the aerosol device according to the invention is the targeted introduction of active ingredients into the hollow cavities in the area of the nose and frontal sinus. Due to anatomical reasons, these areas are poorly supplied with blood and frequently poorly ventilated and therefore active ingredients administered orally or parenterally do not reach the site of action in therapeutically efficacious concentrations. Since the access points are very small and frequently obstructed, preferably only such drug formulations can reach the site that may be transported with aerosol droplets having diameters of less than 10 µm and preferably approximately 2 to 5 µm. The therapeutic action may be improved by the use of surface-active and adhesive excipients in the active ingredient formulations because such excipients improve spreadability and wettability. Recommended to reduce the swelling of the mucous membrane is the application of vasoconstrictive substances before or in combination with anti-inflammatory and anti-allergenic active ingredients, such as for example corticoids and/or antibiotics.

Of the active ingredients which can be of some use for attaining one of these targets are e.g. substances which can be selected from the group of anti-inflammatory drugs, glucocorticoids, antiinfective agents, antibiotics, fungicides, virucides either alone or in combination with biofilm-reducing compounds or inhibitors of efflux pumps, antiseptics, immunomodulators, antioxidents, mycolytica, decongestives, vasoconstrictors, wound-treatment agents, local anesthesics, peptides, proteins and natural or synthetic plant extracts.

Examples of potentially useful anti-inflammatory drugs are steroidal active ingredients such as glucocorticoids such as betamethasone, beclomethasone, budesonide, ciclesonide, dexamethasone, desoxymethasone, fluoconolone acetonide, flucinonide, flunisolide, fluticasone, icomethasone, rofleponide, triamcinolone acetonide, fluocortin butyl, hydrocortisone, hydroxycortisone-17-butyrate, prednicarbate, 6-methylprednisolone aceponate, mometasone furoate and non-steroidal anti-inflammatory drugs (NSAIDs) such as prostaglandine, leukotriene, elastane, bradykinin antagonists, heparin and heparinoide, non-glucocorticoid steroides such as dehdroepiundrostendieone and dehdropianthrosterone (DHEA); any pharmaceutically acceptable salts, esters, isomers, stereoisomers, diasteriomers, epimeres, solvates or other hydrates, prodrugs, derivates or any other chemical or physical forms of the active ingredients which include the corresponding active units.

Examples of antifective agents, the class or therapeutic category of which being understood here such that they include compounds which are effective against bacterial, fungoid and viral infections, i.e. that they include the classes of antimicrobial substances, the antibiotics, fungicides, antiseptics and virucides, either alone or in combination with biofilm-reducing or repressive agents and inhibitors of the efflux pump, are penicillins including benzylpenicillins (penicillin-G-sodium, clemizone penicillin, benzathine penicillin G), phenoxypenicillins (penicillin V, propicillin), aminobenzylpenicillins (ampicillin, amoxycillin, bacampicillin), acylaminopenicillins (azlocillin, mezlocillin, piperacillin, apalcillin), carboxypenicillins (carbenicillin, ticarcillin, temocillin), isoxazolyl penicillins (oxacillin, cloxacillin, dicloxacillin, flucloxacillin), and amiidine penicillin (mecillinam);

cefalosporins including cefazolins (cefazolin, cefazedone); cefuroximes (cerufoxim, cefamdole, cefotiam); cefoxitins (cefoxitin, cefotetan, latamoxef, flomoxef); cefotaximes (cefotaxime, ceftriaxone, ceftizoxime, cefmenoxime); ceftazidimes (ceftadzidime, cefpirome, cefepime); cefalexins (cefalexin, cefaclor, cefadroxil, cefradine, loracarbef, cefprozil), and cefiximes (cefixime, cefpodoxim proxetile, cefuroxime axetil, cefetamet pivoxil, cefotiam hexetil), loracarbef, cefepim, clavulan acid t amoxicillin, ceftobiprole;

synergists including beta-lactamase inhibitors, such as clavulan acids, sulbactam and tazobactam;

cabapenems including imipenem, cilastin, meropenem, doripenem, tebipenem, ertapenem, ritipenam, and biapenem;

monobactams including aztreonam;

aminoglycosides such as apramycin, gentamicin, amikacin, isepamicin, arbekacin, tobramycin, netilmicin, spectinomycin, streptomycin, capreomycin, neomycin, paromoycin and kanamycin;

macrolides including erythromycin, clarythromycin, roxithromycin, azithromycin, dithromycin, josamycin, spiramycin and telithromycin;

gyrase inhibitors or fluroquinolones including ciprofloxacin, gatifloxacin, norfloxacin, ofloxacin, levofloxacin, perfloxacin, lomefloxacin, fleroxacin, garenoxacin, clinafloxacin, sitafloxacin, prulifloxacin, olamufloxacin, caderofloxacin, gemifloxacin, balofloxacin, trovafloxacin and moxifloxacin;

tetracycline including tetracyclin, oxytetracyclin, rolitetracyclin, minocyclin, doxycycline, tigecycline and aminocycline;

glycopeptide including vancomycin, teicoplanin, ristocetin, avoparcin, oritavancin, ramoplanin and Peptid 4;

polypeptides including plectasin, dalbavancin, daptomycin, oritavancin, ramoplanin, dalbavancin, telavancin, bacitracin, tyrothricin, neomycin, kanamycin, mupirocin, paromomycin, polymyxin B and colistin;

sulfonamides including sulfadiazine, sulfamethoxazole, sulfalene, co-trimoxazole, co-trimetrol, co-trimoxazine, co-tetraxazine;

azoles including clotrimazole, oxiconazole, miconazole, ketoconazole, itraconazole, fluconazole, metronidazol, tinidazol, bifonazol, ravuconazol, posaconazol, voriconazol and ornidazol and other fungicides including flucytosin, griseofluvin, tonoftal, naftifin, terbinafin, amorolfin, ciclopiroxolamin, echinocundins, such as micafungin, caspofungin, anidulafungin;

nitrofuranes including nitrofurantoin and nitrofuranzon;

polyenes including amphotericin B, natamycin, nystatin, flucocytosin;

other antibiotics including tithromycin, lincomycin, clindamycin, oxazolindione (linzezolide), ranbezolid, streptogramin A+B, pristinamycin aA+B, virginiamycin A+B, dalfopristin/giunupristin (synercide), chloramphenicol, ethambutol, pyrazinamid, terizidon, dapson, prothionamid, fosfomycin, fucidinic acid, rifampicin, isoniazide, cycloserine, terizidone, ansamycine, lysostaphin, iclaprim, mirocin B17, clerocidine, filgrastim, and pentamidin;

virucides including aciclovir, ganciclovir, birivudin, valaciclovir, zidovudine, didanosin, thiacytidin, stavudin, lamivudin, zalcitabin, ribavirin, nevirapirin, delaviridin, trifluridin, ritonavir, saquinavir, indinavir, foscarnet, amantadin, podophyllotoxin, vidarabin, tromantadin and proteinase inhibitors;

antiseptics including acridine derivatives, iodine providon, benzoates, rivanol, chlorohexetidine, quarternary ammonium compounds, cetrimides, biphenylol, clorofene and octenidine;

plant extracts or components, such as plant extracts of camomile, hamamelis, echiancea, calendula, papain, pelargonium, essential oils, myrtol, pinene, limonene, cineole, thymol, menthol, camphor, tannin, alpha-hederin, bisabol oil, lycopodin, vitapher oil;

wound-treatment compounds including dexpanthenol, allantoin, vitamines, hyaluronic acid, alpha-antitrypsin, inorganic and organic zinc salts/compounds, bismuth salts, interferons (alpha, beta, gamma), tumor necrosis factors, cytokines, interleukines, immunomodulators including methotrexat, azathioprin, cyclosporin, tacrolimus, sirolimus, rapamycin, mofetil, cytostatic agents and metastases inhibitoren, alkylants, such as nimustin, melphanlan, carmustin, lomustin, cyclophosphosphamide, ifosfamide, trofosfamide, chloroambucile, busulfan, treosulfan, prednimustin, thiotepa;

anti-metabolites such as e.g. cytarabin, fluorouracil, methotrexat, mercaptopurin, tioguanin; alkaloids such as vinblastin, vincristin, vindesin; antibiotics such as alcarubicin, bleomycin, dactinomycin, daunorubicin, doxorubicin, epirubicin, idarubicin, mitomycin, plicamycin; complexes of two-group elements (e.g. Ti, Zr, V, Nb, Ta, Mo, W, Pt) such as carboplatinim, cis-platinum and metallocen compounds such as titanocen dichloride; amsacrin, dacarbazin, estramustin, etoposide, beraprost, hydroxycarbamide, mitoxanthron, procarbazin, temiposide; paclitaxel, iressa, zactima, poly-ADP-ribose-polymerase (PRAP) enzyme inhibitors, banoxantron, gemcitabin, pemetrexed, bevacizumab, ranibizumab.

Examples of potentially useful mycolytics are DNase, P2Y2-agonists (denufosol), heparinoides, guaifenesin, acetylcystein, carbocystein, aambroxol, bromhexin, tyloxapol, lecithine, myrtol, and recombined surfactant proteins.

Examples of potentially useful vasoconstrictors which can be useful to reduce swelling of the mucous membrane are phenylephrine, naphazoline, tramazoline, tetryzoline, oxymetazoline, fenoxazoline, xylometazoline, epinephrine, isoprenaline, hexoprenaline and ephedrine.

Examples of potentially useful local anaesthetics contain benzocaine, tetracaine, procaine, lidocaine and bupivacaine.

Examples of potentially useful local antiallergics contain the above-mention glucocorticoids, cromolyn sodium, nedocromil, cetrizin, loratidine, montelukast, roflumilast, ziluton, omalizumab and heparinoids.

Examples of potentially useful peptides and proteins contain antibodies produced from microorganisms against toxins, antimicrobial peptides such as cecropine, defensine, thionine and cathelicidine.

Combinations of any of the above-mentioned active ingredients, which consist of any pharmaceutically acceptable salt, ester, isomer, stereoisomer, diastereomer, epimer, solvate or other hydrate, prodrugs, derivative or any other chemical or physical form of active ingredients, which include the corresponding active units.

The aforementioned substances are preferably used in the form of their common pharmaceutical configurations or as salts, esters, isomers, stereoisomers, diastereomers, epimers, etc., with the objective being in each case to obtain an administrative form that it stable when stored. For this, formulations may be used in a wide variety of administrative forms, for example as solutions, suspensions, emulsions, powders or lyophilisates, etc. in 2-chamber systems with aqueous or non-aqueous solvents or mixtures, etc. It is advantageous to add excipients that improve solubility, for example glycerol, propylene glycol, ethanol, encourage penetration of the paranasal sinuses and frontal sinuses, reduce surface tension and/or prolong the deposition time and dwell time (control release) where appropriate, which may be achieved, for example, by the addition of non-ionic surfactants, for example tyloxapol, vitamin E-TPGS, polysorbates, pluronics, etc. and/or other additives as for example phospholipids, cellulose ether, dextrans, chitosans, cyclodextrines, polyvinylpyrrolidone, polyvinyl alcohol, etc.

Also claimed as inventive is the formulation and application of the aforementioned classes of active ingredients and substances as liposomes, suspensions and emulsions in the micrometer range and preferably in the nanometer range with a geometric diameter of less than approximately 1 µm that are particularly suitable for transportation by small droplets. This ensures that by means of the device according to the invention these preparations are better able to penetrate the paranasal sinuses and frontal sinuses and be deposited and hence develop their action. Active ingredients that have to be used as solid formulations due to their poor storage stability in solution may be either dissolved or suspended with a suitable aqueous or non-aqueous solvent (for example glycerol, propylene glycol, polyglycols, pluronics, ethanol) or mixtures thereof shortly before application. Also claimed is a coating and encasing method to make malodorous or locally irritant substances more tolerable for application by complexation, for example with cyclodextrins. Alternatively, these active ingredients may also be bonded to polymeric excipients, for example chitosan and cellulose ether derivatives or gelatines in order to modify the absorption properties in such a way that the therapeutic effect may be intensified and the application frequency reduced. It is advantageous to use isotonic or hypertonic solutions containing soluble alkali and alkaline-earth salts (for example Emser salts, magnesium chloride, sodium hydrogen carbonate, etc.) and have a physiological pH range (4-9). This may be achieved by the addition of common pharmaceutical buffer substances to the active ingredient formulations. The formulations may also be provided with pharmaceutically common aroma and taste correcting agents to improve their acceptance, particularly as far as children are concerned.

The invention claimed is:

1. Therapeutic aerosol device comprising
    a) a nebulizer device, to which a compressed gas can be supplied, having an aerosol generator for the generation of an aerosol which together with the supplied compressed gas forms a main aerosol flow,
    b) a nosepiece connected with the nebulizer device for supplying the aerosol to one of the two nostrils of the nose of a user,
    c) a flow resistance device for provision of a flow resistance in the other of the two nostril of the user, the flow resistance device having a first opening and a second opening, which is smaller than the first opening, and
    d) a connection device configured for connection to a device for generation of pressure fluctuations, the connection device being formed on the flow resistance device and being configured to introduce the pressure fluctuations into an interior of the flow resistance device between the first and second openings, and being configured to introduce the pressure fluctuations separately from the connection between the nebulizer device and the nosepiece, directly into the respective nostril of the user's two nostrils, such that the pressure fluctuations are superimposed on the main aerosol flow after separate introduction of the main aerosol flow and the pressure fluctuations into the respective nostril of the user to cause the aerosol from the main aerosol flow to reach the paranasal sinuses of the user and to be deposited therein.

2. Therapeutic aerosol device according to claim 1, wherein the flow resistance device comprises the connection device for the supply of pressure fluctuations which extend into the interior of the flow resistance device and further comprises a first opening for the connection of the interior with the nasal cavity of the user.

3. Therapeutic aerosol device according to claim 1, wherein the flow resistance device has a second opening which is designed such that the flow resistance is greater than the flow resistance of the natural flow path through the nasal cavity of the user.

4. Therapeutic aerosol device according to claim 2, wherein the second opening is formed in a wall of the flow resistance device which limits the interior of the flow resistance device.

5. Therapeutic aerosol device according to claim 1, wherein the flow resistance device comprises a stopper to be inserted into the nostril.

6. Therapeutic aerosol device according to claim 5, wherein the stopper is configured in the form of a truncated cone.

7. Therapeutic aerosol device according to claim 1, wherein the flow resistance device is connected by a connecting member with the nosepiece.

8. Therapeutic aerosol device according to claim 1, wherein the frequency of the pressure fluctuations lies within the range from 10 to 100 Hz.

9. Therapeutic aerosol device according to claim 1, wherein the pressure fluctuations are generated by means of a membrane compressor comprising a membrane that seals a pressure chamber in a pressure-tight way and is moved to and fro by a piston rod.

10. Therapeutic aerosol device according to claim 1, wherein the aerosol generator comprises a nebulizer nozzle having a compressed air channel opening up into the nozzle opening and having at least one suction channel through which a liquid to be nebulized is drawn in, the compressed gas supplied to the nebulizer device also effecting the generation of the aerosol.

11. Therapeutic aerosol device according to claim 1, wherein the aerosol generator comprises a membrane aerosol generator and the nebulizer device further comprises a supply device for the supply of the compressed gas to generate a main aerosol flow.

12. Therapeutic aerosol device according to claim 11, wherein the nebulizer device comprises a cylindrical tube piece which is disposed around the expansion spatial area in which the aerosol generated by the aerosol generator spreads, such that the supplied compressed gas impinges on outer sheath surface of the tube piece and flows on a front end into the interior of the tube piece.

13. Therapeutic aerosol device according to claim 12, wherein the cylindrical tube piece is disposed in one of the chambers surrounded by the nebulizer device such that a clearance is formed for the spread of the supplied compressed gas between an outer sheath surface of the cylindrical tube piece and an inner wall surface of the chamber.

14. Therapeutic aerosol device according to claim 12, wherein the front end of the cylindrical tube is located in front of the aerosol generator.

15. Therapeutic aerosol device according to claim 12, wherein the cylindrical tube piece has an annular cylindrical shape.

16. Therapeutic aerosol device according to claim 11, wherein the supply means for the compressed gas comprises a cylindrical connecting piece.

17. Therapeutic aerosol device according to claim 16, wherein the cylindrical connecting piece comprises an outlet directed at the cylindrical tube piece.

18. Therapeutic aerosol device according to claim 17, wherein supply means for the compressed gas comprises a connection device for the connection of a supply line for the compressed gas.

19. Therapeutic aerosol device claim 1, wherein the supply of the compressed gas takes place only at predetermined time intervals.

20. Therapeutic aerosol device according to claim 1, wherein an additional compressed gas flow is added to the supplied pressure fluctuations, which is smaller than the compressed gas flow for the generation of the main aerosol flow.

21. Therapeutic aerosol device according to claim 1, wherein diseases of the upper and lower respiratory tract can be specifically treated if these have a nasal or paranasal cause.

22. Therapeutic aerosol device according to claim 1, wherein the liquid medicinal formulations can thus be particularly advantageously deposited in the paranasal cavities in the form of an aerosol mist in order to treat diseases whose cause is there.

23. Therapeutic aerosol device according to claim 1, wherein, by targeted deposition of the active ingredients in the nose and paranasal cavities, diseases can be topically treated such as chronic or allergic sinusitis, inflammations or infections or other diseases or conditions ("atrophic rhinitis") so as by this means to avoid unwanted side effects or a symptomatic medical therapy.

24. Use of a therapeutic aerosol device according to claim 1, for the application of one or more of the following substances:
    substances selected from the group consisting of anti-inflammatory drugs, glucocorticoids, antiinfective agents, antibiotics, fungicides, virucides either alone or in combination with biofilm-reducing compounds or inhibitors of efflux pumps, antiseptics, immunomodulators, antioxidents, mycolytics, decongestives, vasoconstrictors, wound-treatment agents, local anesthesics, peptides, proteins and natural or synthetic plant extracts;

steroidal active ingredients including glucocorticoids such as betamethasone, beclomethasone, budesonide, ciclesonide, dexamethasone, desoxymethasone, fluoconolone acetonide, flucinonide, flunisolide, fluticasone, icomethasone, rofleponide, triamcinolone acetonide, fluocortin butyl, hydrocortisone, hydroxycortisone-17-butyrate, prednicarbate, 6-methylprednisolone aceponate, mometasone furoate and non-steroidal anti-inflammatory drugs (NSAIDs) including prostaglandin, leukotriene, elastane, bradykinin antagonists, heparin and heparinoide, non-glucocorticoid steroides such as dehdroepiundrostendieone and dehdropianthrosterone (DHEA); any pharmaceutically acceptable salts, esters, isomers, stereoisomers, diasteriomers, epimeres, solvates or other hydrates, prodrugs, derivates or any other chemical or physical forms of the active ingredients which include the corresponding active units;

antifective agents, the class or therapeutic category of which includes compounds which are effective against bacterial, fungoid and viral infections, including the classes of antimicrobial substances, the antibiotics, fungicides, antiseptics and virucides, either alone or in combination with biofilm-reducing or repressive agents and inhibitors of the efflux pump, including penicillins including benzylpenicillins (penicillin-G-sodium, clemizone penicillin, benzathine penicillin G), phenoxypenicillins (penicillin V, propicillin), aminobenzylpenicillins (ampicillin, amoxycillin, bacampicillin), acylaminopenicillins (azlocillin, mezlocillin, piperacillin, apalcillin), carboxypenicillins (carbenicillin, ticarcillin, temocillin), isoxazolyl penicillins (oxacillin, cloxacillin, dicloxacillin, flucloxacillin), amidine penicillin (mecillinam);

cefalosporins including cefazolins (cefazolin, cefazedone); cefuroximes (cerufoxim, cefamdole, cefotiam); cefoxitins (cefoxitin, cefotetan, latamoxef, flomoxef); cefotaximes (cefotaxime, ceftriaxone, ceftizoxime, cefmenoxime); ceftazidimes (ceftadzidime, cefpirome, cefepime); cefalexins (cefalexin, cefaclor, cefadroxil, cefradine, loracarbef, cefprozil), and cefiximes (cefixime, cefpodoxim proxetile, cefuroxime axetil, cefetamet pivoxil, cefotiam hexetil), loracarbef, cefepim, clavulan acid/amoxicillin, ceftobiprole;

synergists including beta-lactamase inhibitors, such as clavulan acids, sulbactam and tazobactam;

cabapenems including imipenem, cilastin, meropenem, doripenem, tebipenem, ertapenem, ritipenam, and biapenem;

monobactams including aztreonam;

aminoglycosides including apramycin, gentamicin, amikacin, isepamicin, arbekacin, tobramycin, netilmicin, spectinomycin, streptomycin, capreomycin, neomycin, paromoycin and kanamycin;

macrolides including erythromycin, clarythromycin, roxithromycin, azithromycin, dithromycin, josamycin, spiramycin and telithromycin;

gyrase inhibitors or fluoroquinolones including ciprofloxacin, gatifloxacin, norfloxacin, ofloxacin, levofloxacin, perfloxacin, lomefloxacin, fleroxacin, garenoxacin, clinafloxacin, sitafloxacin, prulifloxacin, olamufloxacin, caderofloxacin, gemifloxacin, balofloxacin, trovafloxacin and moxifloxacin;

tetracycline including tetracyclin, oxytetracyclin, rolitetracyclin, minocyclin, doxycycline, tigecycline and aminocycline;

glycopeptides including vancomycin, teicoplanin, ristocetin, avoparcin, oritavancin, ramoplanin and Peptid 4;

polypeptides including plectasin, dalbavancin, daptomycin, oritavancin, ramoplanin, dalbavancin, telavancin, bacitracin, tyrothricin, neomycin, kanamycin, mupirocin, paromomycin, polymyxin B and colistin;

sulfonamides including sulfadiazine, sulfamethoxazole, sulfalene, co-trimoxazole, co-trimetrol, co-trimoxazine, co-tetraxazine;

azoles including clotrimazole, oxiconazole, miconazole, ketoconazole, itraconazole, fluconazole, metronidazol, tinidazol, bifonazol, ravuconazol, posaconazol, voriconazol and ornidazol and other fungicides including flucytosin, griseofluvin, tonoftal, naftifin, terbinafin, amorolfin, ciclopiroxolamin, echinocundins, such as micafungin, caspofungin, anidulafungin;

nitrofuranes including nitrofurantoin and nitrofuranzon;

polyenes including amphotericin B, natamycin, nystatin, flucocytosin;

other antibiotics including tithromycin, lincomycin, clindamycin, oxazolindione (linzezolide), ranbezolid, streptogramin A+B, pristinamycin aA+B, virginiamycin A+B, dalfopristin/giunupristin (synercide), chloramphenicol, ethambutol, pyrazinamid, terizidon, dapson, prothionamid, fosfomycin, fucidinic acids, rifampicin, isoniazide, cycloserine, terizidone, ansamycine, lysostaphin, iclaprim, mirocin B17, clerocidine, filgrastim, and pentamidin;

virucides including aciclovir, ganciclovir, birivudin, valaciclovir, zidovudine, didanosin, thiacytidin, stavudin, lamivudin, zalcitabin, ribavirin, nevirapirin, delaviridin, trifluridin, ritonavir, saquinavir, indinavir, foscarnet, amantadin, podophyllotoxin, vidarabin, tromantadin and proteinase inhibitors;

antiseptics including acridine derivatives, iodine providon, benzoates, rivanol, chlorohexetidine, quarternary ammonium compounds, cetrimides, biphenylol, clorofene and octenidine;

plant extracts or components, including plant extracts of camomile, hamamelis, echiancea, calendula, papain, pelargonium, essential oils, myrtol, pinene, limonene, cineole, thymol, menthol, camphor, tannin, alpha-hederin, bisabol oil, lycopodin, vitapher oil;

wound-treatment compounds including dexpanthenol, allantoin, vitamines, hyaluronic acid, alpha-antitrypsin, inorganic and organic zinc salts/compounds, bismuth salts, interferons (alpha, beta, gamma), tumor necrosis factors, cytokines, interleukines, immunomodulators including methotrexat, azathioprin, cyclosporin, tacrolimus, sirolimus, rapamycin, mofetil, cytostatic agents and metastases inhibitoren, alkylants, such as nimustin, melphanlan, carmustin, lomustin, cyclophosphosphamide, ifosfamide, trofosfamide, chloroambucile, busulfan, treosulfan, prednimustin, thiotepa;

anti-metabolites including cytarabin, fluorouracil, methotrexat, mercaptopurin, tioguanin; alkaloids such as vinblastin, vincristin, vindesin; antibiotics such as alcarubicin, bleomycin, dactinomycin, daunorubicin, doxorubicin, epirubicin, idarubicin, mitomycin, plicamycin; complexes of two-group elements (Ti, Zr, V, Nb, Ta, Mo, W, Pt) such as carboplatinim, cis-platinum and metallocen compounds such as titanocen dichloride; amsacrin, dacarbazin, estramustin, etoposide, beraprost, hydroxycarbamide, mitoxanthron, procarbazin, temiposide; paclitaxel, iressa, zactima, poly-ADP-ribose-polymerase (PRAP) enzyme inhibitors, banoxantron, gemcitabin, pemetrexed, bevacizumab, ranibizumab;

mycolytics including DNase, P2Y2-agonists (denufosol), heparinoide, guaifenesin, acetylcystein, carbocystein, aambroxol, bromhexin, tyloxapol, lecithine, myrtol, and recombined surfactant proteins;

vasoconstrictors, which can be useful to reduce swelling of the mucous membrane, are including phenylephrine, naphazoline, tramazoline, tetryzoline, oxymetazoline, fenoxazoline, xylometazoline, epinephrine, isoprenaline, hexoprenaline and ephedrine;

local anaesthetics containing benzocaine, tetracaine, procaine, lidocaine and bupivacaine;

local antiallergics containing the above-mention glucocorticoids, cromolyn sodium, nedocromil, cetrizin, loratidine, montelukast, roflumilast, ziluton, omalizumab and heparinoids;

peptides and proteins containing antibodies produced from microorganisms against toxins, antimicrobial peptides such as cecropine, defensine, thionine and cathelicidine; and combinations of any of the above-mentioned active ingredients, which consist of any pharmaceutically acceptable salt, ester, isomer, stereoisomer, diastereomer, epimer, solvate or other hydrate, prodrugs, derivative or any other chemical or physical form of active ingredients, which include the corresponding active units.

25. Use according to claim 24, wherein the application by the therapeutic aerosol device takes place in such a way that aerosol droplets with a diameter of less than 10 μm are generated.

26. Use according to claim 24, wherein at least one of the substances is used as a liposome, suspension or emulsion in the micrometer range with a geometric diameter of less than 1 μm.

* * * * *